US 6,716,436 B1

(12) United States Patent
Seguin

(10) Patent No.: US 6,716,436 B1
(45) Date of Patent: Apr. 6, 2004

(54) COSMETIC COMPOSITION FOR SLIMMING CONTAINING L-ARGININE, AN L-ARGININE ANALOGUE, OR ONE OF THEIR DERIVATIVES, FOR TOPICAL APPLICATION

(75) Inventor: Marie-Christine Seguin, Monaco (MC)

(73) Assignee: Exsymol S.A.M., Monaco (MC)

( * ) Notice: Subject to any disclaimer, the term of this patent is extended or adjusted under 35 U.S.C. 154(b) by 0 days.

(21) Appl. No.: 09/596,079

(22) Filed: Jun. 16, 2000

(30) Foreign Application Priority Data

Jun. 16, 1999 (FR) .............................. 99 07631

(51) Int. Cl.⁷ .................... A61K 6/00; A61K 9/127; A61K 38/00; A61K 31/21; A61K 31/04
(52) U.S. Cl. .................... 424/401; 424/450; 514/2; 514/63; 514/506; 514/579; 514/740; 514/886; 514/909; 514/912; 514/937; 514/944; 514/945; 514/914
(58) Field of Search ................. 424/401, 450; 514/2, 63, 506, 579, 740, 886, 909, 912, 914, 937, 944, 945

(56) References Cited

U.S. PATENT DOCUMENTS

| | | | | |
|---|---|---|---|---|
| 4,242,329 A | * | 12/1980 | Claeson et al. ............... 514/18 |
| 4,812,555 A | * | 3/1989 | Raddatz et al. ............. 530/323 |
| 4,985,405 A | * | 1/1991 | Gueyne et al. ................. 514/8 |
| 5,364,884 A | * | 11/1994 | Varma et al. ............... 514/551 |
| 5,468,476 A | * | 11/1995 | Ahluwalia et al. ............ 424/73 |
| 5,658,576 A | * | 8/1997 | Soudant ...................... 424/401 |
| 5,792,784 A | * | 8/1998 | Seguin et al. ............... 514/400 |
| 5,821,237 A | * | 10/1998 | Bissett et al. ................. 514/75 |
| 5,830,866 A | * | 11/1998 | Redei et al. .................. 514/12 |
| 5,874,068 A | * | 2/1999 | Engelman et al. ............. 424/54 |
| 6,211,154 B1 | * | 4/2001 | Scarborough et al. ........ 514/18 |
| 6,251,869 B1 | * | 6/2001 | Bohanon ...................... 514/20 |

FOREIGN PATENT DOCUMENTS

| | | |
|---|---|---|
| DE | 43 41 001 | 6/1995 |
| EP | 0 281 435 A1 * | 1/1988 |
| FR | 958 M | 11/1961 |
| FR | 2745498 | 9/1997 |
| FR | 2758724 | 7/1998 |
| GB | 2199243 | 7/1988 |
| WO | WO-88 06034 * | 8/1988 |

* cited by examiner

Primary Examiner—Theodore J. Criares
(74) Attorney, Agent, or Firm—James C. Lydon

(57) ABSTRACT

A cosmetic composition for slimming which includes, in combination with a cosmetically acceptable excipient, at least one compound having the formula (I)

$$\begin{array}{c} \text{(I)} \end{array}$$

where
- $R_1$ is a group bound by a peptidic bond and selected from the group consisting of a hydrogen atom, a hydroxyl group, an acyl group, acyloxy group and a substituted or unsubstituted aminoacid;
- $R_2$ is a group bond by a peptidic bond and selected from the group consisting of a hydroxyl group, an amine group, an alkoxy group, an alkylamine group, a silyloxy group or a substituted or unsubstituted aminoacid; and n is 3 or 4.

14 Claims, No Drawings

COSMETIC COMPOSITION FOR SLIMMING CONTAINING L-ARGININE, AN L-ARGININE ANALOGUE, OR ONE OF THEIR DERIVATIVES, FOR TOPICAL APPLICATION

The present invention concerns a new cosmetic composition for slimming containing L-arginine, an L-arginine analogue, or one of their derivatives, for topical application.

Cosmetic industry is continuously searching for new performing and really efficient active ingredients to fight localised adipose overloads.

Adipose tissue is mainly constituted of adipocytes, which are metabolically very active cells maintaining the energetic balance in the organism by two antagonist metabolic pathways:

lipogenesis, i.e. biosynthesis from glucose and fatty acids, of triglycerides stored into the adipocytes.

lipolysis, which is the hydrolysis of the triglycerides to glycerol and free fatty acids.

Amoung the slimming cosmetic products commercially available are compositions acting by inhibition of lipogenesis, containing inhibitors of glucose uptake or binding which is necessary for the triglycerides synthesis.

Other slimming products aim to stimulate lipolysis by acting on the AMPc level which stimulates the lipase activating the hydrolysis of triglycerides; most of these products contain xanthic bases, especially caffeine, usually associated with vegetal extracts which increase their activity. Some products contain active ingredients which have an action on $\alpha$ and $\beta$ adrenergic receptors which respectively inhibit and stimulate lipolysis.

The influence of sexual hormones and catecholamines on $\beta$-receptors was recently shown, but their use in cosmetic is forbidden.

Recent improvements in understanding the mechanisms of regulation of the adipocyte lead to consider new cosmetic strategies concerning slimming products for topical use.

The new approach described in this patent is the use of a topical lipolytic active ingredient acting on the adipocyte by inducing the release of a cellular mediator.

A researchers team has recently identified a potential regulator of lipolysis: the nitric oxide radical ($NO^\circ$) or its related redox forms (Modulation of White Adipose Tissue Lipolysis by Nitric Oxide, Gaudiot et Coll., J.Biol. Chem., 1998, 273, 13475–13481). It arises from this work that, in an appropriate environment, $NO^\circ$ radical can act as a lipolysis stimulation factor.

Nevertheless, nitric oxide itself or a NO-donor use are not suitable for cosmetic applications.

Actually, nitric oxide radical has many physiologic properties because it is a cellular mediator acting particularly on vascular and neuronal systems.

Nitric oxide is also a potential cellular toxin involved in the immune response. In the skin, $NO^\circ$ takes part in the inflammatory response (for instance during photoinduced stress), modulates melanocytes activity or cellular proliferation in wound healing process.

Furthermore, in some cases, nitric oxide radical can generate in vivo toxic by-products such as peroxinitrous anion.

Thus, one of the aim of the present invention is to solve a part of the above mentioned problems providing a cosmetic composition for slimming, which contains a cosmetic active ingredient able to generate nitric oxide radical in an endogenous way.

L-arginine is the natural substrate of NO-synthase, the enzyme that metabolises arginine to release nitric oxide radical. This enzyme is naturally present in the adipose tissue and maintains a basal level of $NO^\circ$.

Is was shown that an extracellular supply of L-arginine led to $NO^\circ$ production.

Although this enzyme is very specific, it was proved recently that it could accept other substrates, particularly an analogue of L-arginine, homo-L-arginine.

In the scope of this new cosmetic approach, the topical application of the active ingredient was taken in account, which raises the question of its bioavailability that is to say its ability to act on its main biological target: the adipocyte. This kind of cell is not localised in the direct vicinity of the active ingredient application area, but in a deep layer of the skin, hypodermis.

That is why an important aim of the invention is increasing the bioavailability of the cosmetic active ingredient according to the invention.

Thus, one of the characteristics of the cosmetic composition according to the invention is to reduce L-arginine (or its analogue) degradation (by arginases) or metabolisation in skin's upperlayers, or to improve its cutaneous penetration.

NO-synthase is also present in the cells of the upperlayers of the skin, as keratinocytes and fibroblasts.

So an other characteristic of the invention is to avoid any possible side effects that may result from $NO^\circ$ production by skin's upperlayers.

A positive consequence of NO-synthase presence in skin's upperlayers is that the lipolytic composition containing $NO^\circ$ precursor will be able to produce a lipolytic signal which may be transmitted to a deeper layer as hypodermis.

Furthermore, endothelial cells, which form the wall of microvessels irrigating dermis and hypodermis, also have NO-synthases and may contribute to the lipolytic effect. Moreover, they can also help decreasing excess adipose tissue by a special mechanism: $NO^\circ$ can induce a vasodilatation which can promote adipose tissue's draining.

At last, a possible mode of action of nitric oxide radical, suggested by new experimental data, could result from its ability to act against preadipocytes multiplication. Preadipocytes are precursor cells which differentiate in mature adipocytes, able to store fat. This property could fight very efficiently against adipose tissue increase.

The present invention consists in the use of L-arginine, an L-arginine annalogue, or one of their derivatives (or any of their salts) as an endogenous precursor of $NO^\circ$, in cosmetic compositions for slimming with topical application.

So far, L-arginine, L-arginine analogue or their derivatives had never been used as $NO^\circ$ precursor for slimming.

The patent N° FR-A-2.758.724 provides a composition against cellulite and adipose tissue's excess, said composition comprising protamine, a protein containing among other aminoacids arginine. Thus, protamine may have an inhibitory action on fatty acids captation by adipocytes in the subcutaneous adipose tissue. Protamine may act by inhibition of lipogenesis, which is not the effect described in the present invention.

Arginine is also used in the patent N° FR-A-2.745.498 which describes a therapeutic composition associating arginine and silicon used in high-protein low-calorie diets. This composition is orally administrable and aims to improve the effectiveness of a high-protein diet thanks to the lipolytic activity of silicon and to avoid side effects on kidney function with arginine. The patent N° EP-A-0.281.435 relates to a therapeutic product consisting in asilanols-aminoacids complex, said product being appropriate to prepare medicines which are regulators and activators of metabolism, growth and multiplication of some cells. The active agent is the silanol, which biological activity is improved by complexation with a natural aminoacid that can be L-arginine.

Lastly, the use of L-arginine as NO° precursor was described, but the purpose was protecting the tissues from oxidative stress (Cordeiro P. G., Santamaria E, Hu Q. Y. "Use of a nitric oxide precursor to protect pig myocutaneous flaps from ischemia-reperfusion injury"—Plastic & Reconstructive surgery, vol. 102, (1998) n°6, pp. 2040–2048).

The present invention relates to a new cosmetic composition for slimming comprising, in association with any cosmetically acceptable excipient, at least one compound which is L-arginine, an L-arginine analogue or one of their derivatives, or any of their salts, said compound having the following general formula:

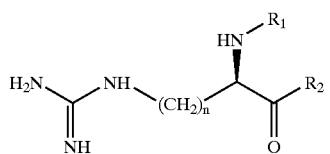

(I)

where:

$R_1$ represents a hydrogen atom, an hydroxyl group, an acyl or acyloxy radical, or an aminoacid substituted or not on its free α-amino function, bound by a peptidic bond, $R_2$ represents an hydroxyl group, an amine, alkylamine or alcoxy radical, a silyloxy group, or an aminoacid substituted or not on its free α-carboxylic function, bound by a peptidic bond, and n is equal to 2 or 3

It is to be noted that the radicals $R_1$ and $R_2$ are biodegradable substituents of the α-amino or α-carboxylic function of L-arginine or its analogue, which can be hydrolyzed in vivo to the corresponding aminoacid.

Considering that L-arginine is the natural substrate of the enzyme NO-synthase, the stereochemistry of the asymmetric carbon of the L-arginine must be respected in all the compounds according to the invention, so that such compounds can be recognized as substrates by NO-synthase.

The compounds of formula (I) that are preferred are the compounds for which $R_1$ represents a hydrogen atom and $R_2$ represents a silyloxy group.

Preferably, the silyloxy group has the following general formula:

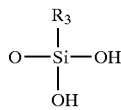

where $R_3$ represents an alkyl group.

In this case, a part of the silanols used to synthesize compound (I) can make a complex or combine by weak bonds with the $NH_2$ group of L-arginine (or its analogue), which contribute to increase the stability of compound (I) and avoid its metabolisation in the upperlayers of the skin.

Among these compounds, a preferred compound is the monomethyl silanediol of L-arginine.

A preferred embodiment of the invention consists in reducing temporarily the polarity of L-arginine or its analogue, so as to favour the active ingredient's penetration in epidermis.

This is simply realised by esterification of the α-carboxylic acid function and/or amidification of the α-amino function, which make these functions non ionizable at a physiologic pH.

The α-carboxylic acid and α-amino substitution by hydrophobic radicals contribute to increase the lipophilicity of the molecule and its cutaneous penetration.

The biodegradability of the substituents, i.e. their ability to hydrolyze at physiological pH or in the presence of cutaneous enzymes, is an important point of the invention because the compounds substituted in alpha position are not biologically active.

Preferably, the α-amino function is substituted by an acetyl radical, or by a more hydrophobic substituent as tert-butyloxycarbonyl (Boc).

Preferably, the α-carboxylic acid function is substituted by a radical $R_2$ alcoxy or alkylamine, carrying an ethyl group or a more hydrophobic substituent as n-butyl, n-octyl radicals, or pivalloyloxymethyl, a substituent which is stable at the external pH of the skin (about pH 5) and hydrolyzed at a pH near to neutrality, that is the pH of the deeper skin's layers.

According to a further preferred embodiment of the invention, the compound of general formula (I) is such as $R_1$ and/or $R_2$ is an aminoacid chosen among the following aminoacids alanine, cysteine, glycine, hydroxyproline, leucine, isoleucine, methionine, phenylalanine, proline, serine, threonine, tryptophane, valine, asparagine, glutamic acid, pyroglutamic acid, aspartic acid, glutamine, arginine, histidine, lysine.

Preferably, the aminoacid is alanine, leucine, isoleucine, phenylalanine, tryptophane or valine which are hydrophobic aminoacids able to increase the lipophilia of the compound in a way to augment its affinity for the skin.

When the radical $R_2$ is an aminoacid, it is better to substitute its free α-carboxylic acid function and/or the free α-amino function of the aminoacid $R_1$ to make this function non ionisable at physiological pH.

Preferably, these functions are substituted by the above mentioned groups.

As it was said, an important aim of the invention is to provide a NO° precursor, the L-arginine or its analogue, which biodisponibility is compatible with an action on hypodermis, a deep layer of the skin.

So it is useful to make a compound having a structure suitable to avoid its metabolisation into the skin's upperlayers before it reaches hypodermis.

This is possible first by substitution of the α-carboxylic acid and α-amino functions of L-arginine. Thus, these forms are biologically inactive (prodrug concept) and will not enter into the metabolic pathways using this aminoacid.

These forms are not substrates of NO-synthases (Hrabak A, Bajor T, Temesi A "Comparison of substrate and inhibitor specificity of arginase and nitric oxide (NO) synthase for arginine analogues and related compounds in murine and rat macrophages"—Biochem. Biophys. Res. Commun., vol. 198, (1994) pp. 206–212).

This resistance to enzymatic deactivation in skin's upperlayers will also be reinforced when the substituents $R_1$ and/or $R_2$ carry a sterically hindering radical.

Thus, when $R_1$ is an acyloxy radical and/or $R_2$ is an alcoxy or alkylamine radical, the alkyl chain carried by these radicals can be an isopropyl, isobutyl, sec-butyl or tertiobutyl group.

Similarly, when $R_1$ and/or $R_2$ is an amino acid, the later is chosen in the group consisting of amino acids having a hindering side chain as valine, leucine or isoleucine.

Following an other embodiment increasing the resistance of compound (I) to enzymatic degradation, $R_1$ and/or $R_2$ radicals are chosen among aminoacids which are substrates of specific enzymes, so that said compound is less sensible to enzymatic deactivation when crossing the upperlayers of the skin.

Such aminoacids can be citrulline, homoserine, norvaline, ornithine, penicillamine or sarcosine.

According to this embodiment, a particularly interesting compound is the natural dipeptide L-citrullinyl-L-arginine (for which $R_1$=citrulline and $R_2$=OH) produced by a red alga (*Chondrus crispus*).

A particularly important aim of the invention, is providing a $NO^°$ precursor which do not induce embarrassing side effect, which is not acceptable for a cosmetic active ingredient.

Thus, as it has been specified, the cosmetic composition according to the invention is conceived in order to avoid $NO^°$ production by the skin's upperlayers cells.

Keratinocytes or fibroblasts normally possess one form of NO-synthase called "constitutive", which produces $NO^°$ in tiny amounts (compatible with $NO^°$'s cellular messenger role) and only in response to very specific stimuli.

However, in some pathologic conditions (specifically inflammation), these cells can express a form of NO-synthase called "inducible", able to produce larger amounts of $NO^°$.

In this context, a particular embodiment of the invention aims to oppose to a toxic by-product of NO radical, peroxinitrous acid (HOONO), which can be produced when skin is submitted to an oxidative stress and which toxicity is increased in the presence of transition metal.

The principle consists in condensing the $NO^°$ precursor on a molecule able to counteract peroxinitrous acid toxicity; said molecule being released during "bioactivation" by cutaneous enzymes.

According to this particular embodiment, a biodegradable substituent $R_1$ or $R_2$, possessing a thiol (SH) or a thioether function, is condensed on L-arginine or its analogue.

In fact, the sulfur atom confers the ability to fix the metallic ions which participate to the formation of cytotoxic species derived from NO radical and therefore to neutralize them.

Moreover, it is known that in vivo, aminoacids possessing a thiol group, particularly cysteine, are preferred target for peroxinitrous acid.

So aminoacids possessing a thiol function chosen among L-cysteine, N-acetyl-cysteine, L-methinonine or penicyllamine will be preferably condensed on L-arginine or its analogue.

Other amino acids are also suitable to avoid possible side effects due to peroxinitrous acid formation, and particularly L-histidine which possesses an imidazole ring having the property to scavenge free radicals which can be generated by peroxinitrous acid (homolytic decomposition releasing $OH^°$ and $NO^°$). Moreover, histidine is known for its chelating properties of transition metals which catalyses toxic reactions associated with peroxinitrous acid.

Advantageously, glutamic acid or aspartic acid can be chosen, which $\alpha$-carboxylic acid functions give them properties of chelation of transition metals.

Cosmetic compositions according to the invention can advantageously contain at least one compound having anti-oxidative properties in order to neutralize free radicals which can be generated by peroxinitrous acid, and to repare damages caused by this species (peroxidizing agent of cellular membranes).

Preferably, this anti-oxidative compound is a pseudo-dipeptide such as the type obtained by the coupling between histamine and an aminoacid and described in the international patent application WO94/19325.

An other particular embodiment of the invention consists in obtaining a composition containing a precursor permitting the endogenous synthesis of $NO^°$ while modifying favourably the redox state of the adipose tissue.

In fact, according to Gaudiot et coll., the lipolytic activity of nitrogen monoxide is modulated by its redox state ($NO^°$, $NO^+$ or $NO^-$); it is particularly appropriated to create a redox state (tissular or intra-cellular) which is going to optimize the lipolytic activity of this messenger.

This can be obtained associating with the compound of general formula (I) an antioxidant as vitamin E (and others related tocopherols), vitamin C (ascorbic acid and derivatives), or a pseudo-dipeptide such as the above mentioned.

It can be advantageously condensed on L-arginine or its analogue a compound having antioxidative properties. Some of these compounds as aminoacids have been already mentioned but cysteine and preferably N-acetyl-cysteine are particularly indicated because their influence on the redox state of the cells has been described.

On the other hand, when the compound of general formula (I) is the monomethylsilanediol of L-arginine, the monomethylsilanediol released during the hydrolysis of the compound can also modulate the cellular redox state in order to maximize the lipolytic effect.

At least, insofar as the subject-matter of the invention consists in bringing to the skin a NO-synthase substrate able to induce endogenous formation of $NO^°$, every additive favouring the activity of this enzyme will be suitable for this purpose.

It has been shown that substances bearing a reduced thiol were necessary for a maximal enzymatic activity.

Thus cystein and other thiol-containing compounds appear as valuable additives.

NADPH can be mentioned, which is a cofactor necessary for the enzyme's activity and which is used during NO formation.

Thus, every substance contributing to the increase of NADPH level in the skin cells will be suitable to favour a NO-dependant lipolytic effect.

Similarly for calcium or every substance enable to increase the intra-cellular calcium level (this element is a cofactor of the enzyme too).

Therefore, monomethylsilanediol of L-arginine is one of the recommended compounds because monomethylsilanediol can favour calcium's supply to the cells (osteoporose treatment).

The compounds of formula (I) can be prepared by methods known by one ordinary skilled in the art.

The cosmetic compositions according to the invention can be used under different forms suitable with cosmetics that is to say solution, emulsion or dispersion, or in the forms of liposomes, microparticles or nanoparticles or even on organic polymers matrix, silica or other mineral medium.

It will be preferably chosen forms enable to favour intradermal penetration as microemulsions, liposomes or Emulzome® which is a fluid microdispersion of fatty compounds/water commercialised by the applicant, having a high bioaffinity for the skin.

The compositions according to the invention can be in any form cosmetically appropriated, and especially in any form suitable for a topical use: cream, milk, lotion, gel, spray, patch.

All the additives and excipients commonly used in cosmetic industry are appropriate to carry out the invention provided they are compatible with compound of formula(I).

Among these additives and excipients can be mentioned: Transcutol® (monomethylic ether: of diethylene glycol), α-Bisabolol, oleic acid or moreover urea. In addition to their specific properties, these last compounds favour the cutaneous penetration.

The following examples will illustrate in a non restrictive way the cosmetic compositions according to the invention.

STRUCTURAL EXAMPLES

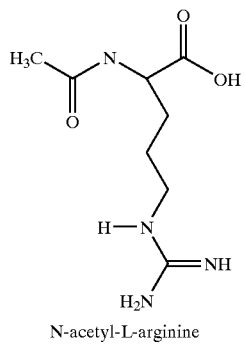
N-acetyl-L-arginine

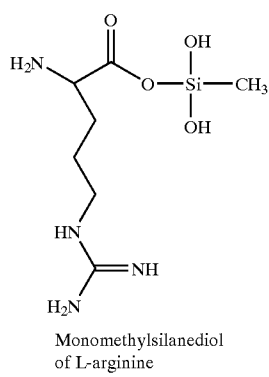
Monomethylsilanediol of L-arginine

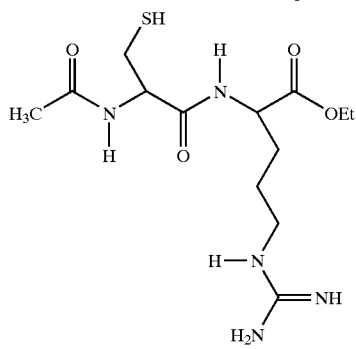
N-acetyl-L-cysteinyl-L-arginine ethylester

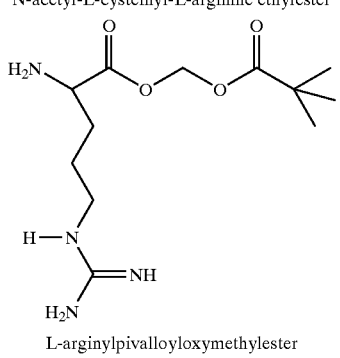
L-arginylpivalloyloxymethylester

Example 1

Fluid Emulsion (Microdisiersion Oil in Water)

| | |
|---|---|
| Sepigel 305 ® | 4.00 g |
| (Polyacrylamide, C13–14 isoparaffine, Laureth-7) | |
| triglycerides of capric and caprillic acids | 5.00 g |
| isopropyle myristate | 5.00 g |
| diheptanoate of neopentyl glycol | 2.00 g |
| glycerin (glycerol) | 5.00 g |
| polyisobutene hydrogenated | 2.15 g |
| cyclomethicone | 0.60 g |
| stearyl heptanoate | 1.43 g |
| imidazolidinyl urea | 0.30 g |
| phenoxyethanol | 0.20 g |
| Monomethylsilanediol of L-arginine | 4.00 g |
| ALISTIN ® (hydroglycolic solution of carcinine chlorhydrate dosed at 10%) | 0.20 g |
| α-bisabolol | 0.50 g |
| disodium EDTA | 0.10 g |
| Water qsp | 100.00 g |

Example 2

Glycolic Gel

| | |
|---|---|
| Carbomer | 0.50 g |
| Transcutol ® (ethoxydiglycol) | 2.00 g |
| Propylene glycol | 1.00 g |
| Sorbitol | 1.00 g |
| Oleth-20 | 1.50 g |
| Phenoxy ethanol | 0.50 g |
| N-acetyl-L-arginine | 5 g |
| Hydroglycolic solution of L-pyroglutamylhistamine dosed at 10% | 0.20 g |
| urea | 3.00 g |
| disodic EDTA | 0.10 g |
| Sodium hydroxide | 0.10 g |
| Eau qsp | 100.00 g |

Example 3

Slimming Cream

| | |
|---|---|
| Sepigel 305 ® (Polyacrylamide, $C_{13-14}$ isoparaffin, Laureth 7) | 2.00 g |
| imidazolidinyl urea | 0.30 g |
| methyl sodium parahydroxybenzoate | 0.10 g |
| propyl parahydroxybenzoate | 0.05 g |
| N-acetyl-L-cysteinyl-L-arginine ethylester | 4.70 g |
| Tegocare 150 (glyceryl stearate, steareth-25, ceteth-20, stearylic alcool) | 10 g |
| cetearyl octanoate | 10.00 g |
| macadamia oil | 10.00 g |
| dimethicone copolyol | 0.30 g |
| dimethicone | 0.20 g |
| glycerin | 3.00 g |
| oleic acid | 1.00 g |
| water qsp | 100.00 g |

Example 4

Slimming Milk

| | |
|---|---|
| Sepigel 501 ® (acrylamide copolymers, paraffin oil, polysorbate-85) | 2.00 g |
| octyl isononanoate | 2.00 g |
| dimethicone copolyol | 0.50 g |
| cetearyl glucoside | 0.80 g |
| polyisobutene hydrogenated | 0.54 g |
| cyclomethicone | 0.15 g |
| stearyl heptanoate | 0.36 g |

| | |
|---|---|
| imidazolidinyl urea | 0.20 g |
| Phanoxyethanol | 0.30 g |
| L-arginylpivalloyloxylmethylester | 3.50 g |
| urea | 1.50 g |
| Water qsp | 100.00 g |

Example 5

Comparative Study of Cutaneous Diffusion

Hairless rats are sacrified by intra-cardiac injection of pentobarbital; the ventral skin is recollected and hypodermis is removed with a scalpel. 0.2 ml by $cm^2$ of the solution to be tested are dropped on a piece of skin (dermis and epidermis) which is set on a diffusion cell. The diffusion is tested in comparison with phosphate buffer containing 0.5% of tween 20.

At different times, the phosphate buffer is replaced and L-arginine is dosed by HPLC in the recollected dialysate fractions.

| Tested products (solution at 30 mM) | % of diffusion after 5h |
|---|---|
| L-Arginine | 15 |
| Monomethylsilanediol of L-Arginine | 42 |
| N-acetyl L-arginine | 47 |
| N-acetyl-L-cysteinyl-L-arginine methylester | 61 |
| L-arginylpivalloyoxymethylester | 51 |

Example 6

Lipolytic Activity in vitro

The in vitro lipolytic activity of solutions containing compounds according to the invention is tested (Solutions at 4%).

The negative control is the solution used for the dilution of the active ingredients ($NH_4HCO_3$ 0.01 M).

The positive controle is caffeine at 1.5 g/l.

Segments of perirenal adipose tissue of male rabbits are incubated in a Krebs-Ringer bicarbonate buffer pH 7.4, which contains 5,5 mM glucose, 40 mg/ml of bovin albumin serum. The total volume of incubation is 3 ml with the substance to be tested prepared in 0.01 M of $NH_4HCO_3$ and additionned in a volume of 0.1 ml. The preparations are stirred at 37° C., under a 95% $O_2$, 5% $CO_2$ atmosphere.

The lipolytic activity levels are quantified by glycerol liberation in the incubation medium and are expressed by gramme of lipid. The glycerol is dosed in duplicate by enzymatic method: glycerokinase, glycerophosphate deshydrogenase (Boerhinger-Mannheim), method of Wieland (32), modified by Vaughan (33).

Results:

| | | Glycerol (nmoles/g of lipids) |
|---|---|---|
| Control | | 0.75 ± 0.3 |
| Monomethylsilanediol of L-arginine | 15 mg/L | 1 ± 0.5 |
| Monomethylsilanediol of L-arginine | 30 mg/L | 2.40 ± 0.35 |
| Monomethylsilanediol of L-arginine | 45 mg/L | 2.5 ± 0.35 |
| Caffeine | 1.5 g/l | 1.45 ± 0.25 |

Example 7

Test in vivo on Rats

Three groups of 4 rats ZUCKER fa/fa defined in an homogeneous way were placed in the animal house at 8 weeks. The experiment begins when the rats have reached 9 weeks and similar weights (240±15 g); they are placed in individual cage with water and food ad libidum. The whole of the rats are circularly hair removed on median part in order to tattoo an axis between the neck and the tail.

On a group N° I, the emulsion described in example 1 is daily applied on the hair-removed part until absorption with removing the excess.

On a group N° II, a ionisation with arginium salicylate at 1% is carried out every two days under 12 volts at the rate of 0.006 $mA/cm^2$ during 7 minutes, with two treating electrodes of 2.5 $cm^2$ laterally fixed on the side of the rat and connected to the positive pole.

A third group is used as the control (group C).

These experiments are carried out during 5 weeks.

The following results show a significant difference in the increase of the adipose mass between treated rats and control rats.

| | Week | | | | | | | | | |
|---|---|---|---|---|---|---|---|---|---|---|
| | 1 | | 2 | | 3 | | 4 | | 5 | |
| | Weight g | Meas mm | Weights g | Meas mm | Weights g | Meas mm | Weights g | Meas mm | Weights g | Meas mm |
| Group C | 275.5 | 187.25 | 315.75 | 214.25 | 347.25 | 237 | 375.5 | 255.75 | 402.5 | 273.25 |
| Group I | 282 | 191.25 | 318.75 | 215 | 347.25 | 232.75 | 368.25 | 245.25 | 386.5 | 254.75 |

-continued

| | Week | | | | | | | | | |
|---|---|---|---|---|---|---|---|---|---|---|
| | 1 | | 2 | | 3 | | 4 | | 5 | |
| | Weight g | Meas mm | Weights g | Meas mm | Weights g | Meas mm | Weights g | Meas mm | Weights g | Meas mm |
| Group II | 280.25 | 189.75 | 318.25 | 213.25 | 345.5 | 224.25 | 367.25 | 233.25 | 386.25 | 238.5 |

WEEKS

— control rats
—·— group <I> rats
······· group <II> rats

MEASUREMENTS
180    200         270   mm

What is claimed is:

1. A cosmetic composition for slimming which comprises, in combination with a cosmetically acceptable excipient, at least one nitric oxide precursor compound which is a L-arginine analogue or one of its derivatives or salts, said compound having the following general formula (I):

$$\underset{NH}{\overset{H_2N}{\diagdown}}\hspace{-4pt}\underset{}{\overset{NH}{\diagup}}\hspace{-6pt}NH-(CH_2)_n-\underset{}{\overset{HN-R_1}{\underset{}{\diagup}}}\hspace{-4pt}\underset{O}{\overset{}{\diagdown}}R_2 \quad (I)$$

wherein:

$R_1$ is selected from the group consisting of
  a hydroxyl group,
  an unsubstituted aminoacid selected from the group consisting of cysteine, hydroxyproline, leucine, isoleucine, methionine, phenylalanine, proline, tryptophan, valine, pyroglutamic acid, histidine, citrulline, homoserine, norvaline, ornithine, penicillamine and sarcosine, and
  an aminoacid substituted on its free α-amino function and selected from the group consisting of cysteine, hydroxyproline, leucine, isoleucine, methionine, proline, tryptophan, valine, pyroglutamic acid, histidine, citrulline, homoserine, norvaline, ornithine, penicillamine and sarcosine,
  said aminoacid being bound by a peptidic bond, $R_2$ is selected from the group consisting of
  an alkoxy group,
  a silyloxy group,
  an unsubstituted aminoacid selected from the group consisting of cysteine, hydroxyproline, leucine, isoleucine, methionine, phenylalanine, proline, tryptophan, valine, pyroglutamic acid, histidine, citrulline, homoserine, norvaline, ornithine, penicillamine and sarcosine, and
  an aminoacid substituted on its free α-carboxylic acid function, and selected from the group consisting of cysteine, hydroxyproline, leucine, isoleucine, methionine, phenylalanine, proline, tryptophan, valine, pyroglutamic acid, histidine, citrulline, homoserine, norvaline, ornithine, penicillamine and sarcosine, said aminoacid being bound by a peptidic bond, and n is 3 or 4.

2. The cosmetic composition of claim 1, wherein n is 3.

3. The cosmetic composition of claim 1, where $R_2$ is a silyloxy group having the following general formula:

$$O-\underset{\underset{OH}{|}}{\overset{\overset{R_3}{|}}{Si}}-OH$$

wherein $R_3$ is an alkyl group.

4. The cosmetic composition of claim 1, wherein said aminoacid is selected from the group consisting of leucine, isoleucine, phenylalanine, tryptophan and valine.

5. The cosmetic composition of claim 1, wherein said aminoacid is selected from the group consisting of methionine, cysteine and histidine.

6. The cosmetic composition of claim 1, wherein $R_2$ is an alkoxy group, said alkoxy group being further substituted with an alkyl radical selected from the group consisting of isopropyl, n-butyl, sec-butyl, tert-butyl, isobutyl, n-octyl and pivalloyloxymethyl.

7. The cosmetic composition of claim 1, further comprising an antioxidant.

8. The cosmetic composition of claim 4, wherein said thiol-containing aminoacid is N-acetyl cysteine.

9. The cosmetic composition of claim 1, further comprising a substance capable of improving the catalytic activity of the NO-synthase enzyme which is either NADPH or calcium.

10. The cosmetic composition of claim 1, wherein said composition is in a form selected from the group consisting of a cream, a milk, a lotion, a gel, a patch and a spray.

11. The cosmetic composition of claim 7, wherein said antioxidant is a member selected from the group consisting of vitamin E, ascorbic acid and a thiol-containing aminoacid.

12. A cosmetic composition for slimming which comprises, in combination with a cosmetically acceptable excipient, at least one nitric oxide precursor compound which is a L-arginine analogue or one of its derivatives or salts, said compound having the following general formula (I):

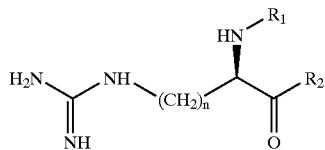

(I)

wherein:

$R_1$ is selected from the group consisting of a hydroxyl group, an unsubstituted aminoacid and an aminoacid substituted on its free α-amino function, said aminoacid being bound by a peptidic bond, $R_2$ is selected from the group consisting of an alkoxy group, a silyloxy group, an unsubstituted aminoacid and an aminoacid substituted on its free α-carboxylic acid function, said aminoacid being bound by a peptidic bond, and n is 3 or 4, and wherein said composition is in a form selected from the group consisting of a cream, a milk, a lotion, a gel, a patch and a spray.

13. The cosmetic composition of claim 1, wherein said compound comprises N-acetyl-L-cysteinyl-L-arginine ethyl ester.

14. The cosmetic composition of claim 1, wherein said compound is at least ones compound selected from the group consisting of L-citrullinyl-L-arginine and L-arginylpivalloyloxy-methylester.

* * * * *